United States Patent [19]

Weetall

[11] 4,111,752

[45] Sep. 5, 1978

[54] COMPARATIVE TEST FOR NEISSERIA

[75] Inventor: Howard H. Weetall, Big Flats, N.Y.

[73] Assignee: Corning Glass Works, Corning, N.Y.

[21] Appl. No.: 837,365

[22] Filed: Sep. 28, 1977

[51] Int. Cl.² .............................................. C12K 1/04
[52] U.S. Cl. ...................... 195/103.5 M; 195/103.5 R
[58] Field of Search .................. 195/103.5 R, 103.5 M

[56] References Cited

U.S. PATENT DOCUMENTS

| | | | |
|---|---|---|---|
| 3,974,269 | 8/1976 | Maley | 195/103.5 A |
| 4,029,756 | 6/1977 | Gaafar | 424/12 |

Primary Examiner—Raymond N. Jones
Assistant Examiner—C. A. Fan

Attorney, Agent, or Firm—Clinton S. Janes, Jr.; Clarence R. Patty, Jr.

[57] ABSTRACT

Bacteria of the genus Neisseria can be detected in a sample by separating a lysate of the sample into two parts, incubating one part with a solution of nicotinamide-adenine-dinucleotide (NAD) and 1,2-propanediol, incubating the other part with a solution of only the NAD, and then comparing the products of each incubation for reduction of NAD to NADH. A difference in NADH concentration indicates the presence of any enzyme specific to Neisseria, this enzyme having the capability of oxidizing 1,2-propanediol and reducing NAD. The structure of the enzyme is not completely understood but, because of those two characterizing properties, the nomenclature 1,2-propanediol dehydrogenase therefor is proposed herein.

10 Claims, No Drawings

COMPARATIVE TEST FOR NEISSERIA

RELATED APPLICATIONS

U.S. patent application Ser. No. 837,366, filed of even date by the present applicant entitled "Detecting Neisseria Bacteria", U.S. patent application Ser. No. 837,364, filed of even date by the present applicant entitled "Detection of Neisseria Bacteria by Immunoassay", U.S. patent application Ser. No. 837,363, filed of even date by the present applicant entitled "Immunoassay of Neisseria Bacteria Via (NH$_4$)$_2$SO$_4$ precipitation", U.S. patent application Ser. No. 837,362, filed of even date by the present applicant entitled "Immunological Detection of Neisseria Bacteria Via Labelled Antibodies", U.S. patent application Ser. No. 837,360, filed of even date by H. C. McDonald entitled "Detection and Quantitation of Neisseria Via Radioimmunoassay of an Enzyme Present in Neisseria Bacteria", and U.S. patent application Ser. No. 837,361, filed of even date by M. M. Takeguchi and the present application entitled "Transport System for Clinical Specimens". Each of those applications is assigned to the assignee of the present application.

BACKGROUND OF THE INVENTION

This disclosure is concerned generally with tests for determining the presence of certain microorganisms and specifically with a test for detecting Neisseria bacteria via a simple enzymatic reaction.

The importance of being able to quickly and accurately detect the presence of Neisseria bacteria, especially Neisseria gonorrhoeae, is well recognized. Present tests for detecting the presence of organisms such as *N. gonorrhoeae* include the preparation of bacteria cultures or the use of serological methods. Such tests, however, have known limitations. See, for example, the publication, "International Symposium on Gonorrhea", B. B. Diena, Ed., a collection of papers presented at the October, 1973 International Symposium on Gonorrhea sponsored by the Health Protection Branch, Health and Welfare Canada, Ottawa, especially at p. 34 et. seq., (1973). A relatively simple and quick enzymatic test for the presence of Neisseria has been discovered and is disclosed in the related application cited above entitled "Detecting Neisseria Bacteria". That test is based on an enzyme assay for an enzyme specific to Neisseria. Thus, that application disclosed the discovery of an enzyme present in Neisseria having the capability of oxidizing 1,2-propanediol and reducing nicotinamide-adenine-dinucleotide (NAD). Although the structure of the enzyme was not fully recognized, the name 1,2-propanediol dehydrogenase was applied thereto and that designation will be employed in this application also.

The inventive method disclosed in the instant specification contemplates a unique application of that basic discovery to simplify the overall procedure. The present test offers many advantages over currently used methods and can be seen from the description below.

SUMMARY OF THE INVENTION

The method of detecting the presence of bacteria of the genus Neisseria in a sample comprises the steps of:
(a) preparing two parts of a lysate of the sample, a first part and a second part;
(b) incubating the first part with a solution of 1,2-propanediol and nicotinamide-adenine-dinucleotide;
(c) incubating the second part with a solution of nicotinamide-adenine-dinucleotide only; and
(d) comparing the incubation products of step (b) with those of step (c) to determine any differences based on the presence or absence of the 1,2-propanediol.

In a very preferred embodiment, a sample or specimen of a human body fluid or exudate (e.g., from a swab) is treated to form a lysate which is then divided into two substantially equal parts. After incubating each part and NAD in the presence or absence of the 1,2-propanediol, the incubation products are monitored for any increase in NADH concentration fluorometrically (excitation 340 nm, emission 460 nm). Alternatively, though less sensitive, a spectrophotometer at 340 nm can be used. A difference in NADH concentration indicates the presence of 1,2-propanediol dehydrogenase and, hence, Neisseria in the sample. Because of the sensitivity of the test, it can be performed using samples having as little as about $2 \times 10^2$ bacteria or less.

SPECIFIC EMBODIMENTS

The method of this disclosure involves three basic steps: the preparation of a sample lysate, incubations of lysate and NAD solutions with and without 1,2-propanediol, and a comparison of the solutions for any significant differences in NADH concentration.

In the first step the sample (e.g., human body fluid or exudate) is subjected to a conventional cellular lysing agent to release intracellular contents, including enzymes. The lysing step need only be under conditions sufficient to avoid denaturing the enzyme of interest.

For the second step, the lysate is divided into two separate parts, a first part and a second part. To avoid corrections or calculations necessary to account for dilution factors, the first and second parts are preferably of equal volume. One sample lysate part is then incubated with an aqueous solution of 1,2-propanediol and NAD. The other lysate part is incubated in a similar solution without the 1,2-propanediol.

For the third step, both incubation solutions (with and without the 1,2-propanediol) are analyzed for NADH concentration. Any significant difference in NADH concentration represents a positive result for the presence of Neisseria in the sample since that difference would be based on the action of the enzyme 1,2-propanediol dehydrogenase from the lysed sample on the 1,2-propanediol + NAD solution, and the inaction of the same enzyme on the solution containing no 1,2-propanediol. Differences in NADH concentration can be monitored coveniently via fluorometry or spectrophotometry.

Any measureable difference is positive for the presence of Neisseria since the only difference in the two incubations is in the incubation substrate. Since NAD can be reduced to NADH only if there is available an enzyme capable of oxidizing the 1,2-propanediol, the comparative test, in showing the presence of 1,2-propanediol dehydrogenase which is specific to Neisseria, is useful for detecting Neisseria in an unknown sample. It is thought that the relative simplicity of a comparative test will permit its use as a practical screening test, especially for *N. gonorrhoeae*.

It can be readily appreciated that, as a practical matter, the sample should be split into two substantially equal parts so that no unnecessary calculations of relative concentrations need be employed. Also, the lysate can be prepared before or after sample splitting although it is more convenient to prepare the lysate prior to sample splitting.

Details of preferred embodiments of the test are given in the following illustrative examples.

EXAMPLE I

Assay Method

To a swab possibly containing the organism is added 1.5 ml 0.1 M Tris, pH 9.0 containing 0.005 M EDTA. EDTA is optionally added to bond divalent metal ions which might interfere with the enzyme. The sample is refrigerated for 60 minutes. The lysate sample is now divided into two equal samples of 0.5 ml each. To one sample is added 2.5 ml 0.1 M TRIS, pH 9.0, containing 100 mg/ml NAD and 3.5% 1,2-propanediol (V/V). To the other sample is added the same solution less the 1,2-propanediol. Both samples are incubated at 50° C. for 60 minutes and then read fluorometrically. The detection of a difference between the two samples of sufficient size indicates the Neisseria bacteria is present.

EXAMPLE II

Sixteen clinical samples were tested for the presence of Neisseria by the comparative method and by conventional culture techniques. The lysis and assay steps were done by placing a swab of unknown sample in 1.5 ml 0.1 M TRIS, pH 9.0 and incubating at 0°–4° C. for 30–60 minutes. Then two 0.5 ml aliquots were taken and placed in separate test tubes. To one tube was added 2.5 ml of 0.1 M Tris, 0.25 M $NH_4Cl$, pH 9.0, containing 10 mg NAD and 100 µl of 1,2-propanediol. To the other tube was added the same solution except for the 1,2-propanediol. Both tubes were incubated at 50° C. for 60 minutes and then read fluoremetrically at 460 nm with stimulation at 340 nm. A difference in fluorometric units (ΔF) of more than 15 was considered positive as indicative of the presence of a 1,2-propanediol dehydrogenase and Neisseria in the swab sample. To assay data are summarized in the Table.

TABLE

| Sample No. | ΔF* | Neisseria Present (+), Absent (−) | |
|---|---|---|---|
| | | Comparative | Culture |
| 1 | 4 | − | − |
| 2 | 0 | − | − |
| 3 | 17 | + | + |
| 4 | 1 | − | − |
| 5 | 3 | − | − |
| 6 | 1 | − | − |
| 7 | 0 | − | − |
| 8 | 2 | − | − |
| 9 | 3 | − | − |
| 10 | 5 | − | − |
| 11 | 0 | − | − |
| 12 | 12 | − | − |
| 13 | 1 | − | − |
| 14 | 23 | + | + |
| 15 | 0 | − | − |
| 16 | 4 | − | − |

*ΔF greater than 15 units considered positive

As can be seen, the comparative test disclosed herein compared quite favorably with conventional culture methods for detecting Neisseria.

Since the test method disclosed herein is subject to numerous modifications, it is intended that the above examples should be construed as illustrative only and that the invention disclosed should be limited only by the claims.

I claim:

1. A method of detecting the presence of bacteria of the genus Neisseria in a sample, the method comprising the steps of:
    (a) preparing two parts identical in composition of a lysate of the sample, a first part and a second part;
    (b) incubating the first part with a solution of 1,2-propanediol and nicotinamide-adenine-dinucleotide;
    (c) incubating the second part with a solution of nicotinamide-adenine-dinucleotide; and
    (d) comparing the incubation products of the reactions of steps (b) and (c) to determine any differences based on the presence or absence of the 1,2-propanediol, which comparison is accomplished by monitoring the concentration of reduced nicotinamide-adenine-dinucleotide.

2. The method of claim 1 wherein the sample is a human body fluid or exudate.

3. The method of claim 1 wherein the lysate of step (a) is prepared from the sample prior to preparing the two parts.

4. The method of claim 1 wherein step (a) includes the additional step of adding a sufficient amount of chelating agent to the two parts to complex with any divalent metal ions in the lysates, which ions might interfere with the incubations of steps (b) and (c).

5. The method of claim 1 wherein the two parts of step (a) are substantially equal in volume.

6. The method of claim 1 wherein the monitoring is done fluorometrically.

7. The method of claim 1 wherein the sample is initially contained on a cotton swab containing, if present, at least about $2 \times 10^2$ Neisseria bacteria.

8. The method of claim 1 wherein the sample, prior to the steps of the test, is contained on a cotton swab containing, if present, at least about $2 \times 10^2$ Neisseria bacteria.

9. The method of claim 1 wherein said Neisseria bacteria are of the species *N. gonnorrhoeae*.

10. A method for detecting the presence of *Neisseria gonorrhoeae* in a sample of human fluid or exudate, the method comprising the steps of:
    (a) preparing two parts identical in composition of a lysate of the sample;
    (b) incubating one part with a solution of 1,2-propanediol and nicotinamide-adenine-dinucleotide;
    (c) incubating the other part with a solution of nicotinamide-adenine-dinucleotide under conditions substantially identical to the incubation of step (b), except for the presence of the 1,2-propanediol;
    (d) monitoring the incubation products of steps (b) and (c) fluorometrically to determine whether the incubation products of step (b) have a higher concentration of reduced nicotinamide-adenine-dinucleotide, thereby indicating the presence of *Neisseria gonorrhoeae* in the sample.

* * * * *